(12) United States Patent
Zhang et al.

(10) Patent No.: US 8,685,428 B2
(45) Date of Patent: *Apr. 1, 2014

(54) THERAPEUTIC COMPOSITION AND A METHOD OF COATING IMPLANTABLE MEDICAL DEVICES

(75) Inventors: Gina Zhang, Fremont, CA (US); Syed F. A. Hossainy, Fremont, CA (US); Eugene Park, Oakland, CA (US); Qi Wang, Sunnyvale, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 328 days.

This patent is subject to a terminal disclaimer.

(21) Appl. No.: 11/602,678

(22) Filed: Nov. 20, 2006

(65) Prior Publication Data

US 2007/0065479 A1 Mar. 22, 2007

Related U.S. Application Data

(63) Continuation of application No. 10/316,739, filed on Dec. 10, 2002.

(51) Int. Cl.
*A61F 2/00* (2006.01)
*A61K 9/14* (2006.01)

(52) U.S. Cl.
USPC .......................................... 424/423; 424/489

(58) Field of Classification Search
None
See application file for complete search history.

(56) References Cited

U.S. PATENT DOCUMENTS

| | | | |
|---|---|---|---|
| 4,081,529 A * | 3/1978 | Crippa ......................... | 514/452 |
| 5,616,595 A | 4/1997 | Chu et al. | |
| 5,843,465 A | 12/1998 | Lundquist | |
| 6,153,217 A | 11/2000 | Jin et al. | |
| 6,322,805 B1 * | 11/2001 | Kim et al. ..................... | 424/426 |
| 6,391,913 B1 * | 5/2002 | Page et al. ..................... | 514/449 |
| 6,395,029 B1 | 5/2002 | Levy | |
| 2002/0051730 A1 * | 5/2002 | Bodnar et al. .................. | 422/33 |
| 2002/0061330 A1 * | 5/2002 | Chowdhary et al. .......... | 424/450 |
| 2002/0173516 A1 | 11/2002 | Chen et al. | |
| 2002/0192294 A1 * | 12/2002 | Albayrak ....................... | 424/501 |
| 2003/0059454 A1 * | 3/2003 | Barry et al. ................... | 424/423 |
| 2003/0064965 A1 * | 4/2003 | Richter ........................ | 514/102 |
| 2004/0117008 A1 | 6/2004 | Wnendt et al. | |
| 2005/0065595 A1 | 3/2005 | Chaplin et al. | |

FOREIGN PATENT DOCUMENTS

WO WO 01/85216 * 11/2001

OTHER PUBLICATIONS

Material Safety Data Sheet, LC Laboratories, Apr. 21, 2009, pp. 1-3.*
Taxotere, Aphios, Aug. 31, 2006, pp. 1-4.*
Liggins, Richard T., et al., Journal of Pharmaceutical Sciences, vol. 86, No. 12, Dec. 1997. pp. 1458-1463.*
Kandadai, Madhuvanthi A., et al., Langmuir, 26(7), (Apr. 6, 2010), pp. 4655-4660.*
Johnson, K.A., et al., Journal of Pharmaceutical Sciences, vol. 76, No. 4 (Apr. 4, 1987) pp. 277-285.*

* cited by examiner

*Primary Examiner* — Scott Long
*Assistant Examiner* — Lyndsey Beckhardt
(74) *Attorney, Agent, or Firm* — Squire Sanders (US) LLP

(57) ABSTRACT

A method of making a therapeutic composition, as well as the therapeutic composition so made, is disclosed. The method comprises mixing a hydrophobic drug with an aqueous buffer solution and adding a surfactant to the aqueous buffer solution to form the therapeutic composition. A implantable medical device with the therapeutic composition and a method of making a coating for an implantable medical device containing the therapeutic composition is also disclosed.

23 Claims, 1 Drawing Sheet

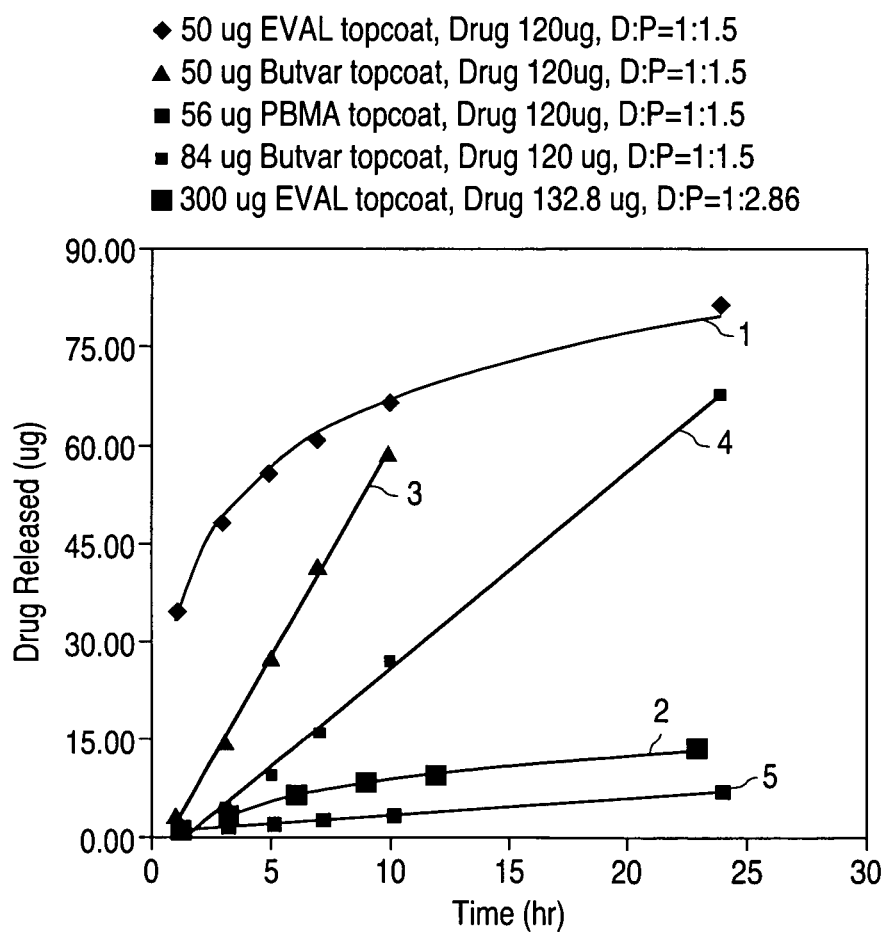

THERAPEUTIC COMPOSITION AND A METHOD OF COATING IMPLANTABLE MEDICAL DEVICES

CROSS REFERENCE TO RELATED APPLICATION

This is a continuation of U.S. application Ser. No. 10/316,739, filed on Dec. 10, 2002, the teachings of which are incorporated hereto by reference in their entirety.

BACKGROUND OF THE INVENTION

1. Field of the Invention

This invention relates to compositions such as those used for coating implantable medical devices such as stents.

2. Description of Related Art

Stents are used not only as a mechanical intervention but also as a vehicle for providing biological therapy. As a mechanical intervention, stents act as scaffoldings, functioning to physically hold open the wall of the passageway. Stents are capable of being compressed, so that they can be inserted through small lumens via catheters, and then expanded to a larger diameter once they are at the desired location. Biological therapy for reducing or eliminating thrombosis or restenosis can be achieved by medicating the stents. Medicated stents provide for the local administration of a therapeutic substance at the diseased site. In order to provide an efficacious concentration to the treated site, systemic administration of such medication often produces adverse or toxic side effects for the patient. Local delivery is a preferred method of treatment in that smaller total levels of medication are administered in comparison to systemic dosages, but are concentrated at a specific site. Local delivery thus produces fewer side effects and achieves more favorable results.

Local delivery can be accomplished by coating the stent with a polymeric carrier containing a biologically active agent. A polymer dissolved in an organic solvent and the agent added thereto are applied to the stent and the organic solvent is allowed to evaporate, leaving a polymeric coating impregnated with the agent.

In the development of drug eluting stents, the rate of release of an active agent from a stent is an important factor which needs to be evaluated. However, the rate of release of agents that have limited solubility in water and are unstable under ambient conditions is difficult to measure. One example of a drug that has proven to be effective for the treatment of restenosis but difficult to calculate the eluting rate from a stent is everolimus (40-O-(2-hydroxy)ethyl-rapamycin) (Novartis Corp.). everolimus, (40-O-(3-hydroxy)propyl-rapamycin, or 40-O-[2-(2-hydroxy)ethoxy]ethyl-rapamycin) are structural derivatives of rapamycin. Rapamycin is an immunosuppressive drug and also possesses antiproliferative properties. Everolimus has a very limited solubility in water, and is, in addition, quite unstable under ambient conditions, posing a serious obstacle for the study of the drug's release kinetics from a stent. In addition, everolimus has limited stability in an aqueous medium.

In view of the foregoing, there is a need to be able to solubilize these types of drugs, and more particularly everolimus, in water and to stabilize these drugs so as to prevent the drugs from degradation in an aqueous environment. Embodiments of the present invention disclose aqueous systems that meet these needs.

SUMMARY

A method of making a therapeutic composition is disclosed, the method comprises mixing a hydrophobic drug with an aqueous buffer solution and adding a surfactant to the aqueous buffer solution to form the therapeutic composition.

A method for fabricating a coating for an implantable medical device, for example a stent, is provided, the method comprises applying a composition to the implantable medical device, the composition comprising a hydrophobic drug mixed with an aqueous buffer solution and a surfactant added thereto.

A therapeutic composition is disclosed; the composition comprises a hydrophobic drug mixed with an aqueous buffer solution and a surfactant added thereto.

BRIEF DESCRIPTION OF THE DRAWINGS

FIG. 1 is a graph showing profiles of a rate of release of everolimus.

DETAILED DESCRIPTION

According to an embodiment of the present invention, hydrophobic drugs such as rapamycin or derivatives or structural or functional analogs thereof, for example, everolimus (40-O-(2-hydroxy)ethyl-rapamycin), can be solubilized and stabilized in an aqueous system by formulating a composition containing the drug and an aqueous carrier. Examples of other hydrophobic drugs that can be used in the practice of the present invention include idoxifene, paclitaxel, estradiol, and 2-methoxyestradiol.

For the purposes of the present invention, the term "hydrophobic" or "hydrophobicity" is defined using the Hildebrand solubility parameter $\delta$. The term "Hildebrand solubility parameter" refers to a parameter measuring the cohesion of a substance and is determined as follows:

$$\delta = (\Delta E/V)^{1/2}$$

where $\delta$ is the solubility parameter, $(cal/cm^3)^{1/2}$;

$\Delta E$ is the energy of vaporization, cal/mole; and

V is the molar volume, $cm^3$/mole.

Hydrophobic compounds typically have a low $\delta$ value. A drug sufficiently hydrophobic to be solubilized, stabilized and used in accordance with the present invention can have a solubility parameter lower than about 11 $(cal/cm^3)^{1/2}$.

The carrier can be de-ionized water or an aqueous buffer solution. The amount of the drug, e.g., everolimus can vary between about 1 and about 100 micrograms (μg) per 1 milliliter (ml) of the aqueous carrier. The buffer solution can be neutral or have a pH ranging from slightly acidic to slightly basic. For example, the buffer solution can have pH between about 6.8 and about 7.8. One example of a suitable buffer solution that can be used is a phosphate buffer saline solution. Examples of alternative buffer solutions that can be used include a carbonate-bicarbonate buffer $H_2CO_3$—$HCO_3^-$, tris-(hydroxymethylamino) ethane (also known as TRIS), piperazine-N,N'-bis-(2-ethanesulfonic acid) (also known as PIPES), N-2-hydroxyethylpiperazine-N'-2-ethanesulfonic acid (also known as HEPES), and 4-(N-morpholino)-butanesulfonic acid (also known as MOBS). TRIS, PIPES, HEPES, and MOBS are available commercially from Sigma-Aldrich Co. of St. Louis, Mo.

The formulation also includes between about 0.01 and about 2.0 mass %, for example, about 1 mass % of a surfactant. The surfactant can be an ionic surfactant, a non-ionic surfactant, or a dual action (Zwitter-ion) surfactant. The surfactant can be a monomer, an oligomer, or a polymer. Examples of suitable surfactants include TRITON X-100, TWEEN 80 and sodium dodecyl sulfate (SDS). Those having ordinary skill in the art will select other appropriate surfactant, if desired.

Examples of alternative surfactants that can be used include non-ionic surfactants such as PLURONIC, alkyl ethoxylates, alkylphenol ethoxylates, glycerol esters, glycol esters, and sugar-based surfactants; anionic surfactants such as soaps, sulfated, sulfonated or phosphated fatty alcohols, and linear alkylbenzene sulfonates; cationic surfactants such as quaternary ammonium salts and alkylated pyridinium salts; and amphoteric surfactants such as betaines and alkylamino oxides.

TRITON X-100 is trade name of a condensate of p-octylphenol with ethylene oxide registered to Rohm & Haas Co. and available from Sigma-Aldrich Co. TWEEN is a trade name of a family of polyoxyethylenesorbitan monooleates registered to, and available from, ICI Americas, Inc. of Bridgewater, N.J. PLURONIC is a trade name of poly(ethylene oxide-co-propylene oxide) registered to, and available from, BASF Corp. of Parsippany, N.J.

The surfactant can form large micelles or vesicles. On contact with the drug, the micelles envelop the molecules of the drug thus solubilizing the drug. The micelles or vesicles also form a protective layer around molecules of the drug shielding the drug from degradation in the aqueous environment. For enhanced protection, for example, against heat or light, additional protecting agents can be optionally added to the system, if desired. Examples of suitable protecting agents include butylated hydroxytoluene and thiopropionic acid.

To prepare an aqueous drug composition, the drug is combined with an aqueous carrier, followed by adding a surfactant and an optional protecting agent to make an aqueous solution of the drug. The composition is heated to a body temperature (about 37° C.) and stirred. A portion of the drug dissolves and remains in the solution, and the remainder does not dissolve and precipitates. The solubility of the drug and the stability of the solution can then be studied. For the purposes of the present invention, the term "solubility" is defined as a fraction of the drug which is dissolved and remains in the aqueous solution.

To conduct the solubility and stability studies, the amount of the drug in the aqueous solution at fixed points in time is measured using a suitable analytical technique, for example, high pressure liquid chromatography (HPLC). For example, the measurements can be done immediately after the solution has been prepared (0 hr time), after 24 hours and 120 hours. The surfactant used to prepare the analyzed solutions can vary. During the experiment, the solution is maintained at about 37° C. Alternatively, the solubility and stability of the everolimus solutions can be conducted using the same surfactant, but varying the amount of the surfactant.

The HPLC method, as any experimental analytical technique is characterized by measurement errors due to imperfections of the equipment and for other reasons. As a result, solubility of everolimus exceeding 100% may be determined in some cases. Those having ordinary skill in the art will understand that in such cases everolimus is completely dissolved.

The solubilized and stabilized drug can be incorporated into a stent coating. The coating can include a drug-polymer layer (referred to as "a reservoir layer") or a drug layer, an optional topcoat layer, and an optional primer layer. The drug-polymer layer can be applied directly onto the stent surface to serve as a reservoir for the drug which is incorporated into the drug-polymer layer. Alternatively, the drug layer comprising the drug and containing no polymer can be applied directly onto the stent surface or onto the primer layer, for example, by applying the drug-containing solution on the stent followed by drying. The topcoat layer can be applied over the drug layer or the reservoir layer. The optional primer layer can be applied between the stent and the reservoir layer or the drug layer to improve the adhesion of the reservoir layer or the drug layer to the stent. The topcoat layer, which can be essentially free from any therapeutic substances or drugs, serves as a rate limiting membrane which further controls the rate of release of the drug.

Poly(ethylene-co-vinyl alcohol) (EVAL) is one example of a suitable polymer than can be employed to prepare the reservoir layer, the optional primer layer, and/or the optional topcoat layer. EVAL has the general formula —[CH$_2$—CH$_2$]$_m$—[CH$_2$—CH(OH)]$_n$—. EVAL is a product of hydrolysis of ethylene-vinyl acetate copolymers. EVAL can also be a terpolymer including up to, for example, 5 molar % of units derived from styrene, propylene and other suitable unsaturated monomers. Other suitable polymers include poly(butyl methacrylate)(PBMA) and polyacetals. One example of a polyacetal that can be used is poly(vinyl butyral-co-vinyl alcohol-co-vinyl acetate) (PVB), for example a brand of PVB manufactured by Monsanto Corp. of St. Louis, Mo. and available from Solutia, Inc. of St. Louis under the trade name BUTVAR. PVB is obtained by hydrolysis of PVA followed by reaction of the polymeric product of hydrolysis with butyraldehyde. Typical brands of BUTVAR can include:

(1) terpolymer having about 80 mass % of vinyl butyral-derived units, about 19 mass % of vinyl alcohol-derived units, and the balance vinyl acetate-derived units;

(2) terpolymer having about 80 mass % of vinyl butyral-derived units and the balance vinyl alcohol-derived units; and (3) terpolymer having about 88 mass % of vinyl butyral-derived units, about 11 mass % of vinyl alcohol-derived units, and the balance vinyl acetate-derived units.

Instead of, or in addition to EVAL, PBMA and BUTVAR, other suitable polymers can be used to fabricate the reservoir layer, the optional primer layer, and/or the optional topcoat layer. Such polymers include poly(hydroxyvalerate), poly(L-lactic acid), poly(glycerol-sebacate), polycaprolactone, poly(lactide-co-glycolide), poly(hydroxybutyrate), poly(hydroxybutyrate-co-valerate), polydioxanone, polyorthoester, polyanhydride, poly(glycolic acid), poly(D,L-lactic acid), poly(glycolic acid-co-trimethylene carbonate), polyphosphoester, polyphosphoester urethane; poly(amino acids), cyanoacrylates, poly(trimethylene carbonate), poly(iminocarbonate), co-poly(ether-esters) (e.g. PEO/PLA), polyalkylene oxalates, polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers other than PBMA, such as copolymers of butyl methacrylate, for instance, with hydroxymethyl methacrylate; vinyl halide polymers and copolymers (such as polyvinyl chloride), polyvinyl ethers (such as polyvinyl methyl ether), polyvinylidene halides (such as polyvinylidene fluoride and polyvinylidene chloride), polyacrylonitrile, polyvinyl ketones, polyvinyl aromatics (such as polystyrene), polyvinyl esters (such as polyvinyl acetate), copolymers of vinyl monomers with each other and olefins (such as ethylene-methyl methacrylate copolymers, acrylonitrile-styrene copolymers, ABS resins, and ethylene-vinyl acetate copolymers), polyamides (such as Nylon 66 and polycaprolactam), alkyd resins, polycarbonates, polyoxymethylenes, polyimides, polyethers, epoxy resins, polyurethanes, rayon, rayon-triacetate, cellulose and its derivatives, cellulose acetate, cellulose butyrate, cellulose acetate butyrate, cellophane, cellulose nitrate, cellulose propionate, cellulose ethers.

The embodiments of the present invention are described with reference to a stent, such as a self-expandable or a balloon expandable stent. Other suitable implantable medical device can also be similarly coated. Examples of such implantable devices include, but are not limited to, stent-grafts, grafts (e.g., aortic grafts), artificial heart valves, cerebrospinal fluid shunts, pacemaker electrodes, and endocardial leads (e.g., FINELINE and ENDOTAK, available from Guidant Corp.). The underlying structure of the device can be of virtually any design. The device can be made of a metallic material or an alloy such as, but not limited to, cobalt chromium alloy (ELGILOY), stainless steel (316L), "MP35N," "MP20N," ELASTINITE (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from Standard Press Steel Co. of Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. Devices made from bioabsorbable or biostable polymers could also be used with the embodiments of the present invention.

Embodiments of the present invention are further illustrated by the following examples:

Example 1

About 600 μg everolimus was mixed with about 100 ml of distilled de-ionized water. The mixture containing about 6.0 μg/ml of everolimus was vigorously stirred while maintained at a temperature of about 37° C. The amount of dissolved everolimus was measured using HPLC immediately after mixing, and then after 24 and 120 hours, while continuing to keep the solution at about 37° C.

About 3.33 μg/ml of everolimus was found in the solution initially, or about 55.5 mass % of the starting amount everolimus mixed with water. After 24 hours, about 0.31 μg/ml was found to remain in the solution, or about 5.2 mass % the starting amount everolimus mixed with water. After 120 hours, no everolimus was found to remain in the solution.

Example 2

About 600 μg everolimus was mixed with about 100 ml of a PBS buffer solution having pH of about 7.4. The mixture was stirred and tested as described in Example 1. About 3.1 μg/ml of everolimus was found in the solution initially, or about 51.7 mass % of the starting amount everolimus mixed with the buffer solution. After 24 hours, about 0.91 μg/ml was found to remain in the solution, or about 15.2 mass % the starting amount everolimus mixed with the buffer solution. After 120 hours, no everolimus was found to remain in the solution.

Example 3

About 600 μg everolimus was mixed with about 100 ml of a PBS buffer solution having pH of about 7.4. The buffer solution contained about 1 mass % of the surfactant TWEEN 80. The mixture was stirred and tested as described in Example 1. About 6.13 μg/ml of everolimus was found in the solution initially, or about 102.1 mass % of the starting amount everolimus mixed with the buffer solution. After 24 hours, about 2.11 μg/ml was found to remain in the solution, or about 35.2 mass % the starting amount everolimus mixed with the buffer solution. After 120 hours, no everolimus was found to remain in the solution.

Example 4

Everolimus was mixed with about the buffer solution as described in Example 3, except instead of TWEEN 80 the buffer solution contained about 1 mass % of the surfactant SDS. The mixture was stirred and tested as described in Example 1. About 0.53 μg/ml of everolimus was found in the solution initially, or about 8.8 mass % of the starting amount everolimus mixed with the buffer solution. After 24 hours, about 0.72 μg/ml was found to remain in the solution, or about 12.0 mass % the starting amount everolimus mixed with the buffer solution. After 120 hours, about 1.02 μg/ml was found to remain in the solution, or about 17.0 mass % the starting amount everolimus mixed with the buffer solution. The increase of the amount of everolimus can be attributed to an interplay of solubility everolimus in an aqueous system containing SDS and stability of the aqueous everolimus solution in the presence of SDS. Since stabilizing of the everolimus solution may take time, more everolimus in the solution may be detected at later point in time.

Example 5

Everolimus was mixed with about the buffer solution as described in Example 3, except instead of TWEEN 80 the buffer solution contained about 1 mass % of the surfactant TRITON X-100. The mixture was stirred and tested as described in Example 1. About 6.17 μg/ml of everolimus was found in the solution initially, or about 102.8 mass % of the starting amount everolimus mixed with the buffer solution. After 24 hours, about 5.42 μg/ml was found to remain in the solution, or about 90.3 mass % the starting amount everolimus mixed with the buffer solution. After 120 hours, about 3.36 μg/ml was found to remain in the solution, or about 56.0 mass % the starting amount everolimus mixed with the buffer solution.

Examples 1-5 can be summarized as shown by Table 1.

TABLE 1

The solubility and stability test results
(the amount of everolimus combined with an aqueous carrier is about 6.0 µg/ml,
temperature about 37° C.)

| Example | Carrier | Surfactant and amount, | Amount of everolimus found in solution at 0 hour | | Amount of everolimus found in solution at 24 hours | | Amount of everolimus found in solution at 120 hours | |
|---|---|---|---|---|---|---|---|---|
| | | | µg/ml | % of initial amount as measured | µg/ml | % of initial amount as measured | µg/ml | % of initial amount as measured |
| 1 | Water | N/A | 3.33 | 55.5 | 0.31 | 5.2 | 0.00 | 0.00 |
| 2 | PBS, pH = 7.4 | N/A | 3.10 | 51.7 | 0.91 | 15.2 | 0.00 | 0.00 |
| 3 | PBS, pH = 7.4 | TWEEN 80, 1% | 6.13 | 102.1 | 2.11 | 35.2 | 0.00 | 0.00 |
| 4 | PBS, pH = 7.4 | SDS, 1% | 0.53 | 8.80 | 0.72 | 12.0 | 1.02 | 17.0 |
| 5 | PBS, pH = 7.4 | TRITON X-100, 1% | 6.17 | 102.8 | 5.42 | 90.3 | 3.36 | 56.0 |

Example 6

About 250 µg everolimus was mixed with about 100 ml of a PBS buffer solution having pH of about 7.4. The buffer solution contained about 1 mass % of the surfactant TRITON X-100. The mixture was stirred and tested as described in Example 1. About 2.42 µg/ml of everolimus was found in the solution initially, or about 96.8 mass % of the starting amount everolimus mixed with the buffer solution. After 24 hours, about 2.14 µg/ml was found to remain in the solution, or about 85.6 mass % of the starting amount of everolimus mixed with the buffer solution.

Example 7

Everolimus was mixed with the buffer solution as described in Example 6, except instead of about 1 mass % of TRITON X-100, the buffer solution contained about 0.1 mass % of TRITON X-100. The mixture was stirred and tested as described in Example 1. About 2.30 µg/ml of everolimus was found in the solution initially, or about 92.0 mass % of the starting amount everolimus mixed with the buffer solution. After 24 hours, about 1.83 µg/ml was found to remain in the solution, or about 73.2 mass % the starting amount everolimus mixed with the buffer solution.

Example 8

Everolimus was mixed with the buffer solution as described in Example 6, except instead of about 1 mass % of TRITON X-100, the buffer solution contained about 0.01 mass % of TRITON X-100. The mixture was stirred and tested as described in Example 1. About 2.17 µg/ml of everolimus was found in the solution initially, or about 86.8 mass % of the starting amount everolimus mixed with the buffer solution.

After 24 hours, about 0.58 µg/ml was found to remain in the solution, or about 23.2 mass % the starting amount everolimus mixed with the buffer solution.

Examples 6-8 can be summarized as shown by Table 2.

TABLE 2

The solubility and stability test results
(the amount of everolimus combined with a PBS buffer is about 2.5 µg/ml,
pH of the buffer is about 7.4, temperature about 37° C.)

| Example | Surfactant and amount | Amount of everolimus found in solution at 0 hour | | Amount of everolimus found in solution at 24 hours | |
|---|---|---|---|---|---|
| | | µg/ml | % of initial amount | µg/ml | % of initial amount |
| 6 | TRITON X-100, 1% | 2.42 | 96.8 | 2.14 | 85.6 |
| 7 | TRITON X-100, 0.1% | 2.30 | 92.0 | 1.83 | 73.2 |
| 8 | TRITON X-100, 0.01% | 2.17 | 86.8 | 0.58 | 23.2 |

Example 9

An aqueous composition containing everolimus, PBS buffer and TRITON X-100 surfactant can be prepared as described in Example 6. The composition can contain about 2.5 µg/ml of everolimus, and about 1 mass % of TRITON X-100.

A first polymer composition can be prepared by mixing the following components:

(a) about 4.0 mass % of EVAL; and (b) the balance, DMAC (dimethylacetamide) solvent.

The first polymer composition can be applied on the surface of a bare stent by spraying, dried, and baked at about 140° C. for 2 hours, to form a primer layer. A spray coater can be used, having a 0.014 inch fan nozzle maintained at about 60° C. with a feed pressure of about 0.3 atm (about 3 psi) and an atomization pressure of about 1.35 atm (about 20 psi). About 20 µg per coating pass can be applied and the total amount of solids of the primer layer can be about 100 µg. "Solids" means the amount of the dry residue deposited on the stent after all volatile organic compounds (e.g., the solvent) have been removed.

A second polymer composition can be prepared by mixing the following components:

(c) about 4.0 mg of EVAL;

(d) about 1,600 ml of the aqueous everolimus-containing composition described above; and (e) about 92 mg of a solvent mixture, the mixture containing DMAC and pentane where the mass ratio between DMAC and pentane would be 8:2.

The above described second polymer composition can contain about 4 mg of pure everolimus. The polymer composition can be applied onto the dried primer layer by spraying, dried, and baked at about 50° C. for about two hours, to form the drug-polymer layer. A spray coater can be used, having a 0.014 inch fan nozzle maintained at about 60° C. with a feed pressure of about 0.2 atm (about 3 psi) and an atomization pressure of about 1.35 atm (about 20 psi). The total amount of solids of the drug-polymer layer can be about 240 μg, including about 120 μg of everolimus and about 120 μg of EVAL.

A third polymer composition can be prepared by mixing the following components:

(f) about 2.0 mass % of EVAL; and (g) the balance, DMAC.

The third polymer composition can be applied onto the dried drug-polymer layer by spraying and dried, to form the topcoat layer on each stent. The total solids weight of the topcoat layer can be about 50 μg.

Example 10

A stent can be coated as described in Example 9, except the drug-polymer layer can contain about 132.8 μg of everolimus and the total solids weight of the topcoat layer can be about 300 μg.

Example 11

A stent can be coated as described in Example 9, except the polymer used to fabricate the drug-polymer and the topcoat layers can be BUTVAR.

Example 12

A stent can be coated as described in Example 11, except the total solids weight of the topcoat layer can be about 84 μg.

Example 13

A stent can be coated as described in Example 9, except the polymer used to fabricate the drug-polymer and the topcoat layers can be PBMA, and the total solids weight of the topcoat layer can be about 56 μg.

Example 14

A first polymer composition was prepared by mixing the following components:

(a) about 4.0 mass. % of EVAL; and (b) the balance, DMAC solvent.

The first polymer composition was applied on the surface of a bare stent by spraying, dried, and baked at about 140° C. for 2 hours, to form a primer layer. A spray coater was used, having a 0.014 inch fan nozzle maintained at about 60° C. with a feed pressure of about 0.3 atm (about 3 psi) and an atomization pressure of about 1.35 atm (about 20 psi). About 20 μg per coating pass was applied and the total amount of solids of the primer layer was about 100 μg.

A second polymer composition was prepared by mixing the following components:

(c) about 4.0 mass % of EVAL;

(d) about 1.0 mass % of everolimus; and (e) the balance, a solvent mixture containing DMAC and pentane where the mass ratio between DMAC and pentane was 8:2.

The second polymer composition was applied onto the dried primer layer by spraying, dried, and baked at about 50° C. for about two hours, to form the drug-polymer layer. A spray coater was used, having a 0.014 inch fan nozzle maintained at about 60° C. with a feed pressure of about 0.2 atm (about 3 psi) and an atomization pressure of about 1.35 atm (about 20 psi). The total amount of solids of the drug-polymer layer was about 240 μg, including about 120 μg of everolimus and about 120 μg of EVAL.

A third polymer composition was prepared by mixing the following components:

(f) about 2.0 mass % of EVAL; and (g) the balance, DMAC solvent.

The third polymer composition was applied onto the dried drug-polymer layer by spraying and dried, to form the topcoat layer. The total solids weight of the topcoat layer was about 50 μg.

Example 15

A stent was coated as described in Example 14, except the drug-polymer layer contained about 132.8 μg of everolimus and the total solids weight of the topcoat layer was about 300 μg.

Example 16

A stent was coated as described in Example 14, except the polymer used to fabricate the drug-polymer and the topcoat layers was BUTVAR.

Example 17

A stent was coated as described in Example 16, except the total solids weight of the topcoat layer was about 84 μg.

Example 18

A stent was coated as described in Example 14, except the polymer used to fabricate the drug-polymer and the topcoat layers was PBMA, and the total solids weight of the topcoat layer was about 56 μg.

Some of the parameters of the stent coatings fabricated according to Examples 14-18 are summarized in Table 3.

TABLE 3

| Stent Coatings of Examples 14-18. | | | |
|---|---|---|---|
| | Amount of everolimus in drug- | Topcoat layer | |
| Example | polymer layer, μg | Polymer | Amount, μg |
| 9 | 120 | EVAL | 50 |
| 10 | 132.8 | EVAL | 300 |
| 11 | 120 | BUTVAR | 50 |
| 12 | 120 | BUTVAR | 84 |
| 13 | 120 | PBMA | 56 |

The rate of release of everolimus from the stents coated according to Examples 14-18 was studied by immersing the stents in an aqueous medium and measuring the amount of everolimus released as a function of time. The aqueous medium was prepared by dissolving about 10 g of TRITON X-100 in about 1 liter of the PBS buffer having pH of about 7.4. The amount of everolimus released was measured chromatographically.

The rate release profiles are shown by FIG. 1. On FIG. 1, curve 1 shows the release profile for a stent coated according to Example 14, curve 2 shows the release profile for a stent coated according to Example 15, curve 3 shows the release profile for a stent coated according to Example 16, curve 4 shows the release profile for a stent coated according to Example 17, and curve 5 shows the release profile for a stent coated according to Example 18.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method comprising:
    (a) mixing everolimus with an aqueous buffer solution or water thereby forming a mixture of everolimus and the aqueous buffer solution or a mixture of everolimus and water; and
    (b) adding a surfactant to the mixture to form a composition, wherein an amount of everolimus being mixed with the aqueous buffer solution or water is between about 1 and 100 micrograms per milliliter of the buffer solution or water;
    wherein the surfactant is selected from a group consisting of a condensate of p-octylphenol with ethylene oxide, sodium dodecyl sulfate, and a polyoxyethylenesorbitan monooleate;
    whereby the surfactant forms micelles or vesicles which envelop everolimus molecules; wherein the micelles or vesicles consist of the surfactant, everolimus, and the aqueous buffer solution or water.

2. The method of claim 1, wherein the composition is used for coating a stent.

3. The method of claim 1, wherein the aqueous buffer solution is a phosphate buffer solution.

4. The method of claim 1, wherein the aqueous buffer solution has a pH between about 7.0 and 7.5.

5. The method of claim 1, wherein the surfactant is a condensate of p-octylphenol with ethylene oxide or sodium dodecyl sulfate.

6. The method of claim 1, wherein an amount of the surfactant added to the buffer solution is between about 0.01 mass % and about 2.0 mass % of the buffer solution.

7. A composition prepared by a method comprising:
    (a) mixing everolimus with an aqueous buffer solution or water thereby forming a mixture of everolimus and the aqueous buffer solution or a mixture of everolimus and water, and
    (b) adding a surfactant to the mixture to form a composition,
    wherein an amount of everolimus mixed with the aqueous buffer solution or water is between about 1 and 100 micrograms per milliliter of the buffer solution or water;
    wherein the surfactant is selected from a group consisting of a condensate of p-octylphenol with ethylene oxide, sodium dodecyl sulfate, and a polyoxyethylenesorbitan monooleate;
    wherein the surfactant forms micelles or vesicles which envelop everolimus molecules; wherein the micelles or vesicles consist of the surfactant, everolimus, and the aqueous buffer solution or water.

8. The composition of claim 1, wherein the aqueous buffer solution is a phosphate buffer solution.

9. The composition of claim 1, wherein the aqueous buffer solution has a pH between about 7.0 and 7.5.

10. The composition of claim 1, wherein the surfactant is a condensate of p-octylphenol with ethylene oxide or sodium dodecyl sulfate.

11. The composition of claim 1, wherein an amount of the surfactant added to the buffer solution is between about 0.01 mass % and about 2.0 mass % of the buffer solution.

12. An implantable medical device comprising the composition of claim 1.

13. An implantable medical device comprising the composition of claim 8.

14. An implantable medical device comprising the composition of claim 9.

15. An implantable medical device comprising the composition of claim 10.

16. An implantable medical device comprising the composition of claim 11.

17. A method for fabricating a coating for an implantable medical device comprising the step of applying the composition of claim 1.

18. A method for fabricating a coating for an implantable medical device comprising the step of applying the composition of claim 8.

19. A method for fabricating a coating for an implantable medical device comprising the step of applying the composition of claim 9.

20. A method for fabricating a coating for an implantable medical device comprising the step of applying the composition of claim 10.

21. A method for fabricating a coating for an implantable medical device comprising the step of applying the composition of claim 11.

22. The method of claim 1, wherein the amount of everolimus being mixed with the aqueous buffer solution or water is between about 1 and 10 micrograms per milliliter of the buffer solution or water.

23. The Composition of claim 1, wherein the amount of everolimus being mixed with the aqueous buffer solution or water is between about 1 and 10 micrograms per milliliter of the buffer solution or water.

* * * * *

UNITED STATES PATENT AND TRADEMARK OFFICE
CERTIFICATE OF CORRECTION

| | | |
|---|---|---|
| PATENT NO. | : 8,685,428 B2 | Page 1 of 1 |
| APPLICATION NO. | : 11/602678 | |
| DATED | : April 1, 2014 | |
| INVENTOR(S) | : Gina Zhang | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 330 days.

Signed and Sealed this
Sixth Day of September, 2016

Michelle K. Lee
*Director of the United States Patent and Trademark Office*